US010285650B2

(12) United States Patent
Faisal et al.

(10) Patent No.: US 10,285,650 B2
(45) Date of Patent: May 14, 2019

(54) HEART MONITORING DEVICE AND METHOD

(71) Applicant: Imperial Innovations Limited, London (GB)

(72) Inventors: Aldo Faisal, London (GB); Constantinos Gavriel, London (GB)

(73) Assignee: IMPERIAL INNOVATIONS LIMITED, London (GB)

( * ) Notice: Subject to any disclaimer, the term of this patent is extended or adjusted under 35 U.S.C. 154(b) by 0 days.

(21) Appl. No.: 15/112,717

(22) PCT Filed: Jan. 20, 2015

(86) PCT No.: PCT/GB2015/050126
§ 371 (c)(1),
(2) Date: Jul. 20, 2016

(87) PCT Pub. No.: WO2015/107374
PCT Pub. Date: Jul. 23, 2015

(65) Prior Publication Data
US 2016/0338648 A1    Nov. 24, 2016

(30) Foreign Application Priority Data
Jan. 20, 2015  (GB) .................................. 1400928.6

(51) Int. Cl.
*A61B 5/11*    (2006.01)
*A61B 5/024*    (2006.01)
(Continued)

(52) U.S. Cl.
CPC ........ *A61B 5/6898* (2013.01); *A61B 5/02438* (2013.01); *A61B 5/0404* (2013.01);
(Continued)

(58) Field of Classification Search
CPC . A61B 5/6898; A61B 5/02438; A61B 5/0404; A61B 5/1102; A61B 5/6823;
(Continued)

(56) References Cited

U.S. PATENT DOCUMENTS

2004/0243005 A1    12/2004  Rapps
2011/0066042 A1     3/2011  Pandia et al.
(Continued)

FOREIGN PATENT DOCUMENTS

WO    2010145009 A1    12/2010
WO    2012112407 A1     8/2012
(Continued)

OTHER PUBLICATIONS

Kwon, S. et al., "Validation of Heart Rate Extraction Through an iPhone Accelerometer," Engineering in Medicine and Biology Society, EMBC, 2011 Annual International Conference of the IEEE, Aug. 30, 2011, pp. 5260-5263.

*Primary Examiner* — Paula J Stice
(74) *Attorney, Agent, or Firm* — William J. Clemens; Shumaker, Loop & Kendrick, LLP

(57) ABSTRACT

A mobile telecommunications device arranged for monitoring the heart of a human or an animal includes at least one sensor for measuring an effect of heart function and producing a signal indicative of the effect, and a processor arranged to receive the signal and analyze it and to produce an output indicating a condition of the heart. A method of diagnosis of heart disease includes measuring an effect of heart function using one or more sensors, producing a signal indicative of the effect, and using a processor to receive the signal and analyze it and to produce an output indicating a condition of the heart.

15 Claims, 6 Drawing Sheets

(51) Int. Cl.
*A61B 5/00* (2006.01)
*A61B 5/0404* (2006.01)
*A61B 5/0402* (2006.01)

(52) U.S. Cl.
CPC .......... *A61B 5/1102* (2013.01); *A61B 5/6823* (2013.01); *A61B 5/725* (2013.01); *A61B 5/7207* (2013.01); *A61B 5/7282* (2013.01); *A61B 5/0402* (2013.01); *A61B 2503/40* (2013.01); *A61B 2562/0219* (2013.01)

(58) Field of Classification Search
CPC ..... A61B 5/7207; A61B 5/725; A61B 5/7282; A61B 5/0402; A61B 2503/40; A61B 2562/0219
See application file for complete search history.

(56) References Cited

U.S. PATENT DOCUMENTS

| | | | |
|---|---|---|---|
| 2012/0203124 A1 | 8/2012 | Lim | |
| 2012/0220835 A1* | 8/2012 | Chung | A61B 5/0022 600/301 |
| 2012/0266648 A1* | 10/2012 | Berme | G01L 25/00 73/1.08 |
| 2013/0072145 A1 | 3/2013 | Dantu | |

FOREIGN PATENT DOCUMENTS

| | | | |
|---|---|---|---|
| WO | 2014036436 A1 | 3/2014 | |
| WO | 2014042845 A1 | 3/2014 | |

* cited by examiner

HEART MONITORING DEVICE AND METHOD

FIELD OF THE INVENTION

The present invention relates to devices and methods for monitoring the human or animal heart, for example by measuring the heart rate.

BACKGROUND OF THE INVENTION

Cardiovascular diseases are the number one cause of death in civilized nations and according to recent research performed by World Health Organisation they account for more than 30% of all global deaths. Ischaemic heart disease, high blood pressure, arteriosclerosis, atherosclerosis and angina pectoris are just a very small list of irreversible heart disorders that affect people worldwide. By the time they are detected, the underlying cause is usually quite advanced and has progressed for several years. Unfortunately this problem delays and complicates treatment and in many cases it is impossible for patients to fully recover. Consequently there is a clear emphasis on detection and proper treatment of cardiovascular problems at a very early stage.

Electrocardiography (ECG) is the standard heart monitoring and diagnosis technique that allows easy measurement of the rate and regularity of heartbeats. However, ECG requires external electrodes to be attached to the surface skin of chest and also relatively expensive signal amplifiers to extract a decent signal for subsequent analysis. On the other hand, cardiovascular clinical research often depends on the understanding of the mechanical functionality of the heart, something which the electrical signal generates only limited information about.

An alternative to ECG is Ballistocardiography (BCG), in which mechanical movement of the body caused by the pumping of the heart is measured. BCG devices have been incorporated into daily life objects like beds, chairs or even modified weighing scales. More recently, seismocardiography (SCG) was introduced where sensors are directly attached on the human or animal chest to record chest vibrations. These known techniques provide an off-line solution for heart signal analysis and require dedicated, often bulky equipment.

The rapid evolution in smartphone technology observed in the last couple of years has equipped smartphones with features useful to users in their everyday activities and thus has undoubtedly made smartphones an important part of our daily life, Smartphone sales are increasing every year and currently there is 24% penetration on a worldwide scale, something that is estimated to reach 45% by 2016.

SUMMARY OF THE INVENTION

The present invention provides a device for monitoring the heart of a human or animal comprising at least one sensor for measuring a heart characteristic or an effect of heart function and producing a signal indicative of the heart characteristic or effect, a processor arranged to receive the signal and analyze it and to produce an output indicating a condition or parameter of the heart or heart function. The device may further comprise a memory for storing data relating to the signal and/or the output. The device may comprise a mobile telecommunications device, for example a smartphone. The device may be placed on the chest of a patient and may be operable to produce an output comprising a ballistocardiographic heart signal.

Advantageously, the device gives the patient an indication of a condition of the heart. In its simplest form, the output may simply be a measurement of the heart rate. In more sophisticated embodiments, the output can include a suggested diagnosis of a heart disease. The device can be used to prompt the patient to seek medical treatment while making the data available to medical staff for preliminary diagnosis. Further, the use of smartphones provides small and portable medical equipment, instantly available to millions of patients around the world.

Further, the present invention provides a computer readable medium including instructions which when operated on a smartphone are arranged to cause the smartphone to operate as a device for monitoring the heart. In a particularly advantageous aspect, the computer readable medium can comprise a downloadable mobile application or "app", whereby the invention can be widely disseminated at low cost. Additionally, the invention can advantageously be directly deployed to existing hardware without any additional hardware costs.

The at least one sensor may comprise at least one motion sensor to produce a motion signal. The motion sensor can comprise an accelerometer arranged to produce an acceleration signal. Three accelerometers can be provided, wherein each is arranged to produce an acceleration signal. The processor may be arranged to analyze the acceleration signal or signals to determine or extract information concerning the heart condition. The processor may be arranged to generate from the motion signals a three-dimensional motion signal from which to extract information concerning the heart condition. Advantageously, the device can thus be placed in any orientation against the patient's chest and the chest motion measured along a set of three axes, and from the information thus gathered, the heart condition can be assessed.

Where data is gathered by measuring motion of the patient's chest, the acceleration signal may includes a component due to the breathing of the patient and the processor may be arranged to remove the signal component due to breathing so that the heart condition can be accurately measured. For example the processor can be arranged to remove the breathing component using a smoothing algorithm, such as a Savitzky-Golay smoothing algorithm.

A maximum value of the acceleration signal may be considered to represent a heart beat and the processor may therefore be arranged to identify maxima in the acceleration signal. The processor may be arranged to scan a fixed or variable time window of the signal and identify maxima in the window. One way to identify a maximum is by identifying a first-occurring peak above a cut-off value for the window. The cut-off value may be determined from the signal in the time window. For example it may be calculated dependent on at least one of the mean and standard deviation of the signal within the window. The cut-off value can be given by $\mu+2.5\sigma$, where $\mu$ is the mean of the signal and a is its standard deviation. Alternatively, the cut-off value can be expressed in terms of the median value of the signal and the interquartile range. After a peak has been identified, the processor can be arranged to shift the fixed time window to a time interval after the peak and to identify the next peak in the shifted window.

The present invention further provides a method of diagnosis of heart disease comprising measuring a heart characteristic using one or more sensors, and producing a signal corresponding to the heart characteristic, using a processor to receive the signal and analyse it and to produce an output indicating a condition of the heart, and storing data relating to the signal and/or the output in a memory.

The invention also provides a computer readable medium including instructions which when operated on a smartphone are arranged to cause the smartphone to perform the method just described.

The invention additionally provides a method of testing a device in accordance with the invention, the method comprising contemporaneously recording an electrocardiographic (ECG) heart signal of a human or animal and a ballistocardiographic (BCG) signal of the human or animal using the device according to the invention and comparing the ECG and BCG signals.

DESCRIPTION OF THE DRAWINGS

The device, or method, may further comprise any one or more features of the embodiments of the invention which will now be described by way of example only with reference to the accompanying drawings, in which.

DETAILED DESCRIPTION OF THE INVENTION

Figure 1:
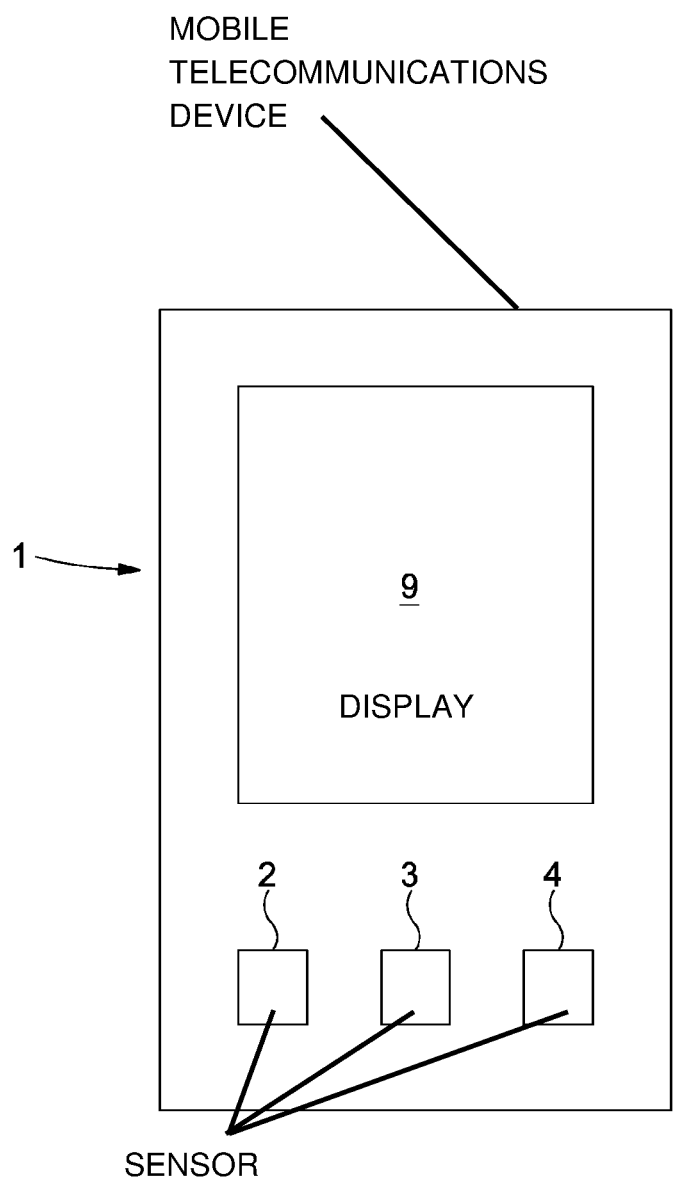
FIG. 1 shows a device according to an embodiment of the invention.
Figure 2:
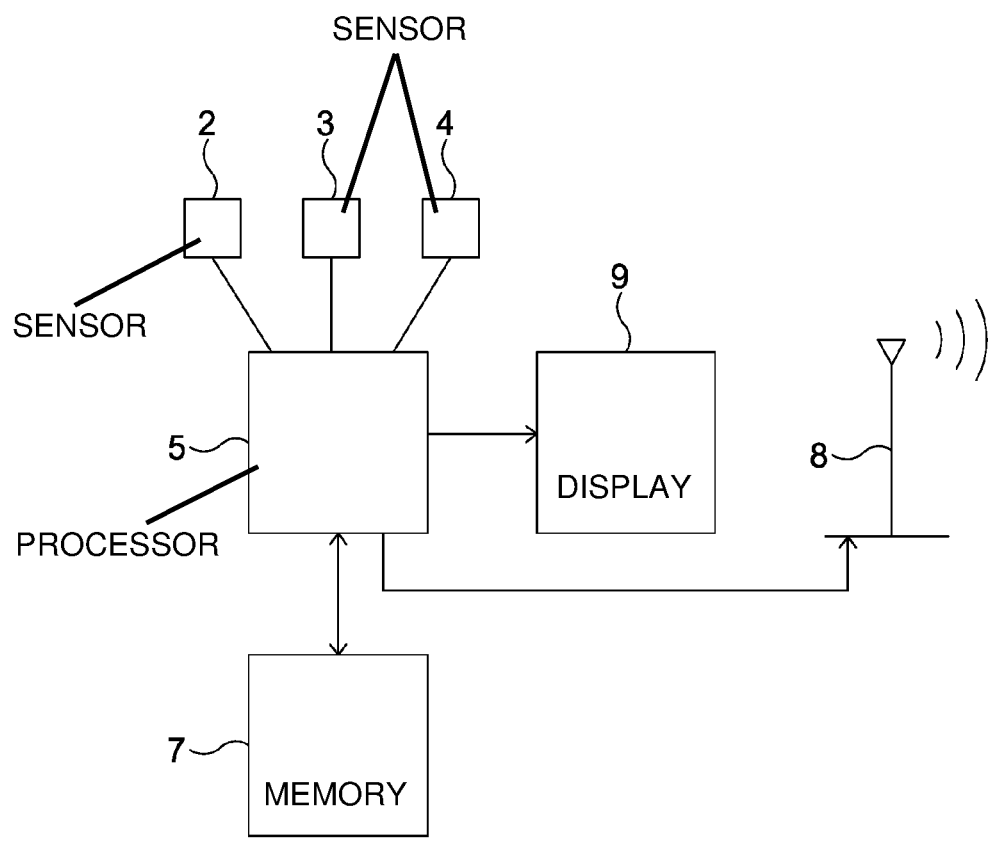
FIG. 2 shows schematically some of the components of the device shown in FIG. 1.

Referring to FIG. 1, a mobile telecommunications device 1 comprises a smartphone including at least three sensors 2, 3, 4 as well as a display 9. The sensors 2, 3, 4 comprise motion sensors, e.g. accelerometers and are arranged to measure acceleration in respective mutually orthogonal directions, and output an acceleration signal indicative of the acceleration it is measuring. Referring to FIG. 2, the accelerometers 2, 3, 4 are connected to a processor 5, which is arranged to process the acceleration signals output by the accelerometers. A memory 7 is also connected to the processor for storing data relating to the sensor signals and/or the output. The processor 5 is also connected to the display 9, and is arranged to control the display to provide various outputs, whereby the user can view results produced by the device. The device also includes an antenna 8 which allows the output to be transmitted over a wireless communications network if desired.

Figure 3:
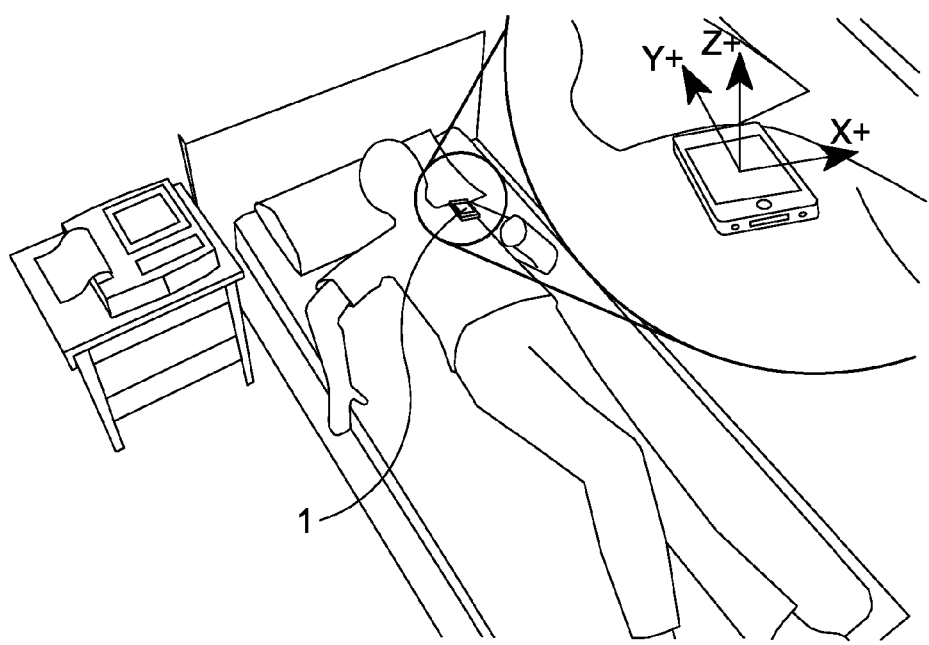
FIG. 3 illustrates a way in which the device can be used.

Referring to FIG. 3, in use, the device 1 is placed on the user's chest while the user is lying down and the device records chest acceleration data along x, y and z axes defined in relation to the device.

Ballistocardiography generally refers to an arbitrary mechanical signal related to cardiovascular activity, e.g. from a suspension bed or similar. There are two preferred placement positions for the smart phone device to obtain physiologically meaningful signals for the ballistocardiography. The first, straightforward option is that the device should be placed onto the surface of the chest, directly above the heart. However chest morphology can affect the signal depending on gender and body fat composition by either having a dampening effect on the signal or lead to instability of the otherwise loosely placed device. Therefore the equivalent alternative placement options is on the sternum (breastbone), closest located to heart, but sufficiently far away that gentle tapping with the finger yields a firm tactile impression of the bone. This placement is equivalent to the first placement region above the heart, as the rigid mechanical bone structure transmits well the mechanical signal that is captured by the device.

Figure 4:
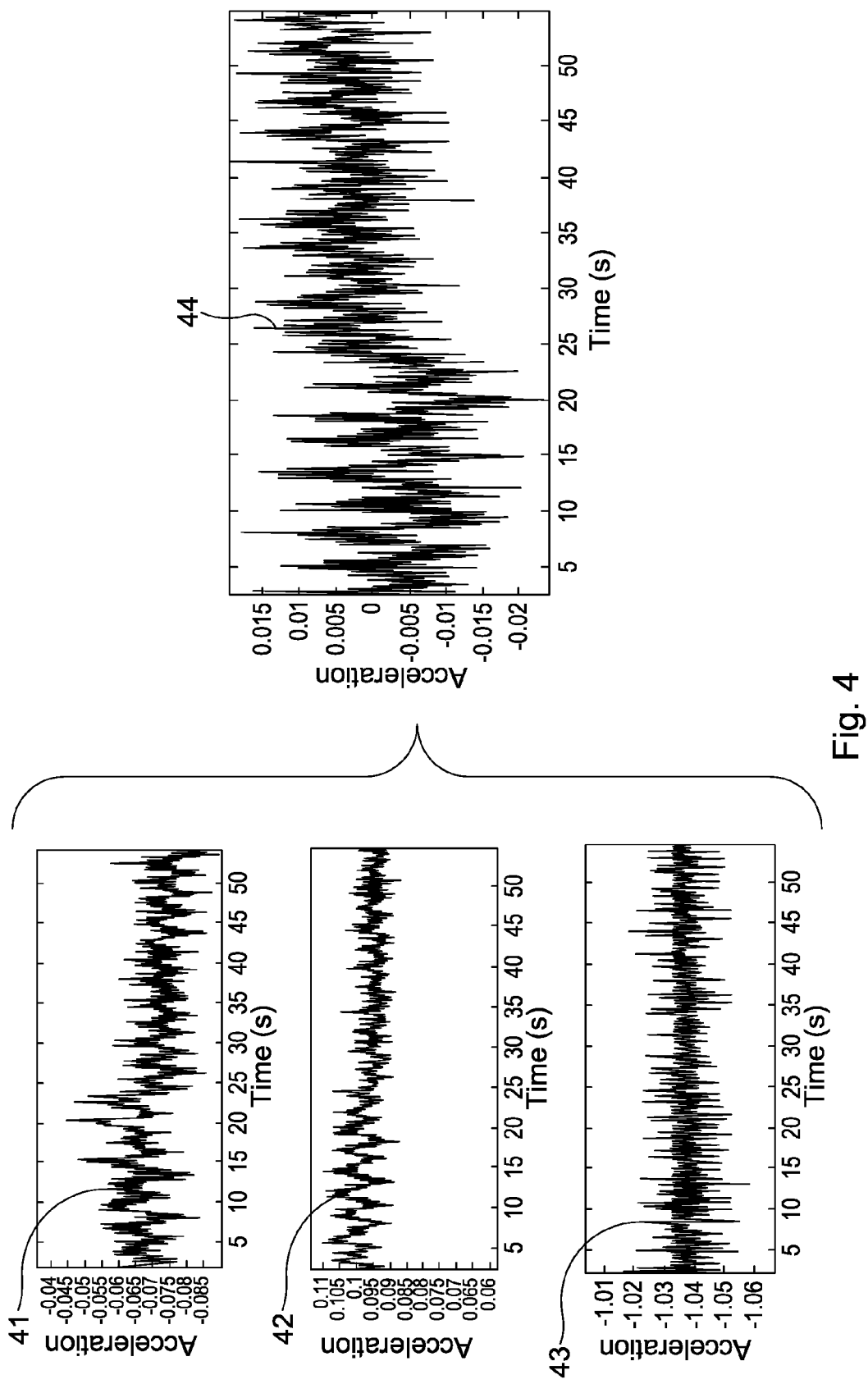
FIG. 4 shows a signal that is produced by the device.

Referring to FIG. 4, the result of the measurement is a set of three motion or, in particular, acceleration signals shown on the left hand side of the Figure. In this embodiment of the invention, raw accelerometer data for each individual axis is produced and stored, including acceleration along the x-axis 41, acceleration along the y-axis 42 and acceleration along the z-axis 43. The processor 5 is arranged to analyze the three signals and to produce a single acceleration signal 44 from the data contained in the original three signals. The preferred way of doing this is to use principle component analysis (PCA). A 10-second window of accelerometer data is preferably used for this analysis, to generate in real time a single accelerometer signal representing the acceleration on the axis with the most variance. By virtue of this technique, the outcome of the measurement is largely independent of the position and orientation of the device relative to the user's chest.

The processor is arranged to extract and store raw data for all three accelerometer axes at a 100 Hz sampling rate. The processor is arranged to optimise live data streaming architectures for analysing data as efficiently as possible and also making them directly available to an external source for further analysis. Additionally for overcoming smartphone limited processing capabilities, multi-threading technology can be used to allow the collection and processing of all data in parallel without worrying about losing any incoming data from the sensors.

Analyzing the collected accelerometer signal on a smartphone with limited resources, is not a trivial problem. Where the smartphone is an Apple iPhone, Apple's Accelerate Framework can be used to assist with efficiently handling computationally intensive algorithms for signal analysis.

Figure 5:
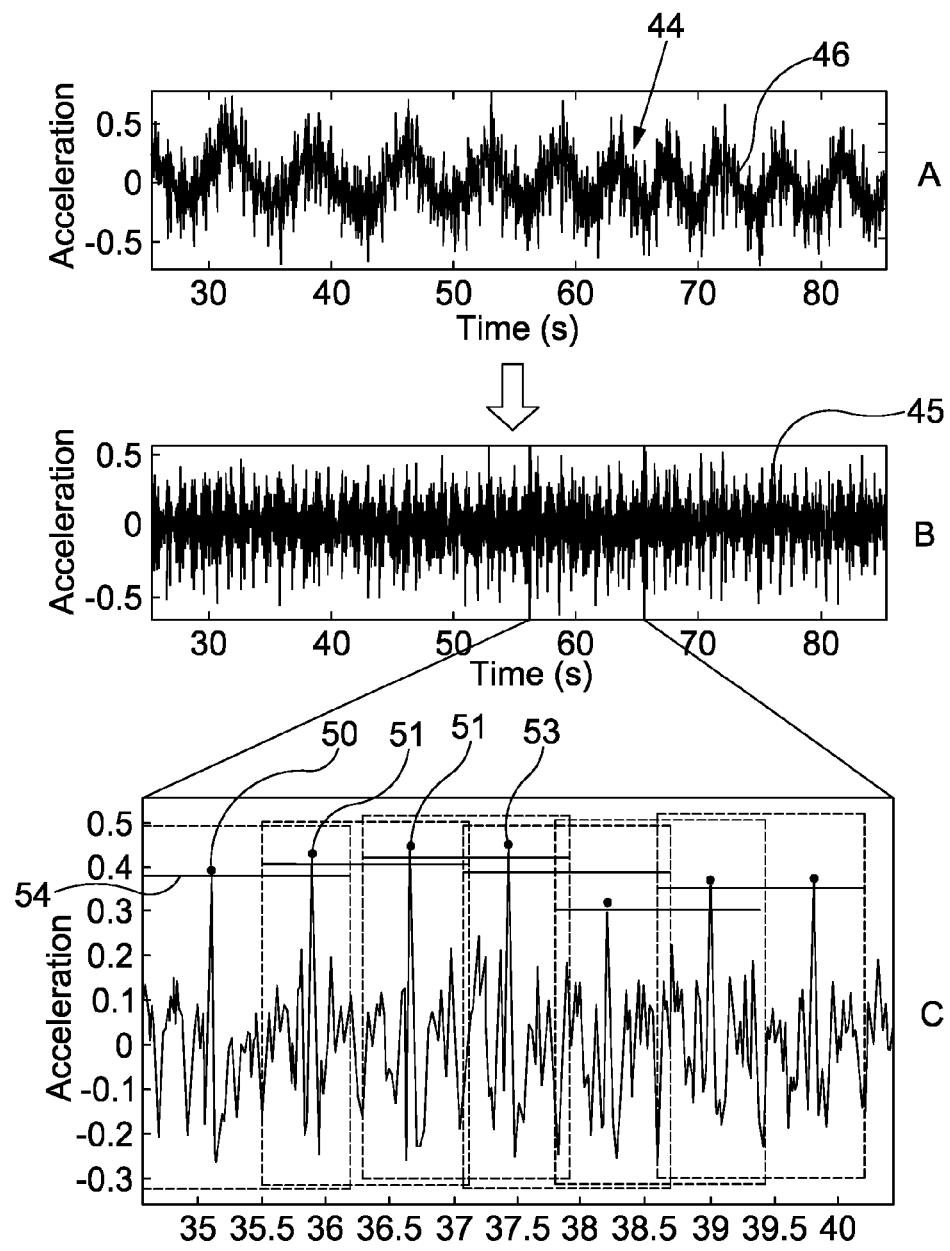
FIG. 5 illustrates some of the signal processing used to produce an output.

Referring to FIG. 5A, when the device is used on a subject, an acceleration signal 44 is generally produced which includes accelerometer data affected by breathing. The effect of the breathing can be removed as will be described below, and FIG. 5B shows the acceleration signal 45 after such removal.

A variety of algorithms for extracting the heart beat intervals from the accelerometer signal in real-time have been tested, ranging from Fast Fourier Transform (FFT) to static and adaptive running window algorithms. The device has been found to be most efficient where the processor is arranged to perform an algorithm that uses an adaptive fixed-size running window as shown in FIG. 5C.

According to this algorithm, the processor dynamically stores the last 3 seconds of data in the memory 7 and swipes over the data using a fixed window of 1.7 secs, representing a heart rate of 35 bpm which is the lowest achievable heart rate in normal conditions. Then the processor uses the data within a window to detect sharp acceleration changes, and specifically to identify any peaks in acceleration within the window that exceed a threshold value. As soon as a peak 50 is found, the window is shifted to the peak point found and additionally a small deviation of approximately 0.2 seconds is added to avoid picking the same point again. The shifted window is therefore arranged to start at, or within a fixed period after, the time of the peak found in the previous window. The device then checks for a new heart beat 51 in the shifted window, and the peak detection and window shifting repeated to identify all of the relevant peaks in the signal. The maximum value repeats quasi-periodically, which can be attributed to the natural variation in the heart rate. Detecting the heart beat by just selecting the maximum point within each window would cause problems when the window is wide enough to include two heart-beat points. Having identified the second peak 51, the processor then again shifts the window and identifies third and fourth peaks 52, 53 and so on.

In the adaptive fixed-size running window algorithm a statistical approach is used to avoid misidentification of heart beats, using the mean and standard deviation of the collected signal to estimate a cut-off threshold value. This cut-off value 54, is given by $\mu+2.5\sigma$, where $\mu$ is the mean of the signal and a is the standard deviation and it represents an area where 97.9% of the accelerometer time-points lay below that value and only the very large peaks exceed it. Therefore by selecting the first occurring peak point above the threshold, it is ensured that no peaks are missed. In an alternative, the cut-off value can be calculated using a median value of the signal and the interquartile range of the signal.

The removal of the breathing component of the signal is dealt with as follows. When the subject inhales, the chest surface moves further away from the heart and this reduces the strength of acceleration signals picked up by the sensors. Moreover, the smartphone orientation is altered by the breathing motion and this results in a smooth cyclic variation in the acceleration signal as shown by line 46 in FIG. 5A.

To extract breathing artifacts from the accelerometer data without affecting the signal, the processor is arranged to implement a detrending filter based on a Savitzky-Golay smoothing algorithm. According to the algorithm, the processor performs a local 3rd order polynomial regression on a window of 300 points to determine a smoothed value for each point, resulting in a new signal which is breathing-free, as shown in FIG. 5B. This signal can now be analysed to determine the heart condition as described above. An alternative to the Savitzky-Golay method is to use a high pass filter that allows the heart signal to pass, but removes the low-frequency breathing signal. It will be appreciated that other filtering methods can be used to remove the breathing component of the acceleration signals.

Figure 6:
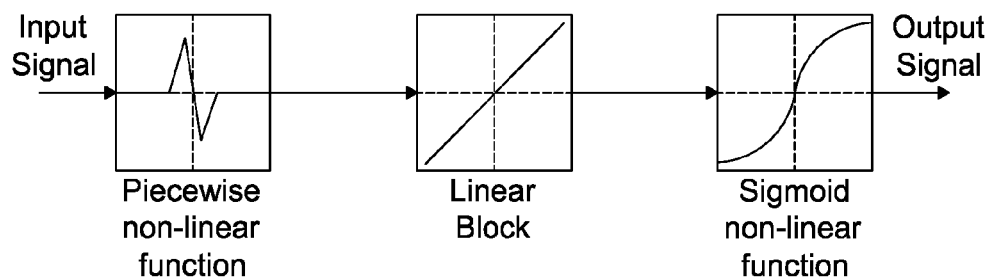
FIGS. 6 and 7 illustrate a comparison of a signal produced using the device with an ECG signal.

In order to test the accuracy of the device, an ECG has been used alongside the device for comparison of the independent results. Mapping the BCG to the ECG signal, one option is to apply a Wiener filter, which is mainly used in signal processing applications for reducing the amount of noise in a signal by comparing it with an estimation of is equivalent noiseless signal. In the present case, the ECG signal is acting as the noiseless signal and a model needed to be developed to reduce the noise in BCG signal. However, the main issue with Wiener filter is the assumption that signals and noise are stationary linear stochastic processes with known spectral characteristics, something that is not true for our signals as the heart rate is changing over time. To overcome this problem a Hammerstein-Weiner filter has been used, which is based on the original Wiener filter but it has the advantage of supporting static non-linear subsystems and linear dynamic systems. The Hammerstein-Weiner filter consists of a linear mapping block surrounded by two non-linear blocks as shown in FIG. 6. The most efficient model that achieves the highest matching between estimated ECG and actual ECG signal is designed using a linear block with zero delay that decomposes the signal into smaller linear components and two Piecewise nonlinear functions.

The experiments for testing the effectiveness of the iPhone accelerometers were performed in a quiet lab. The experiments also involved the use of an electrocardiogram device, to obtain a reference signal for evaluating the accuracy of the heart rate estimation algorithms. The ECG device sampled the subject ECG signal at 1000 Hz and then the collected signal was down sampled to 100 Hz to match the average smartphone accelerometer sampling rate and thus make further analysis steps easier. Seven healthy subjects participated in the experiments and were placed lying on a bed with the ECG clips attached to their left and right wrists and above the ankle of their right leg. Next the smartphone was placed on their chest roughly above the heart area as shown in FIG. 1. Both ECG and smartphone devices were calibrated and the collected signals were timewise aligned. From each subject 5 minutes of data was collected while being at rest, breathing normally without talking and trying to limit their movements as much as possible.

Using the data collected from the subjects during the experiments, the efficiency of the BCG-based heart-rate extraction algorithm was estimated and also the effectiveness of the Hammerstein-Weiner model for converting the BCG to ECG signal.

Figure 7:
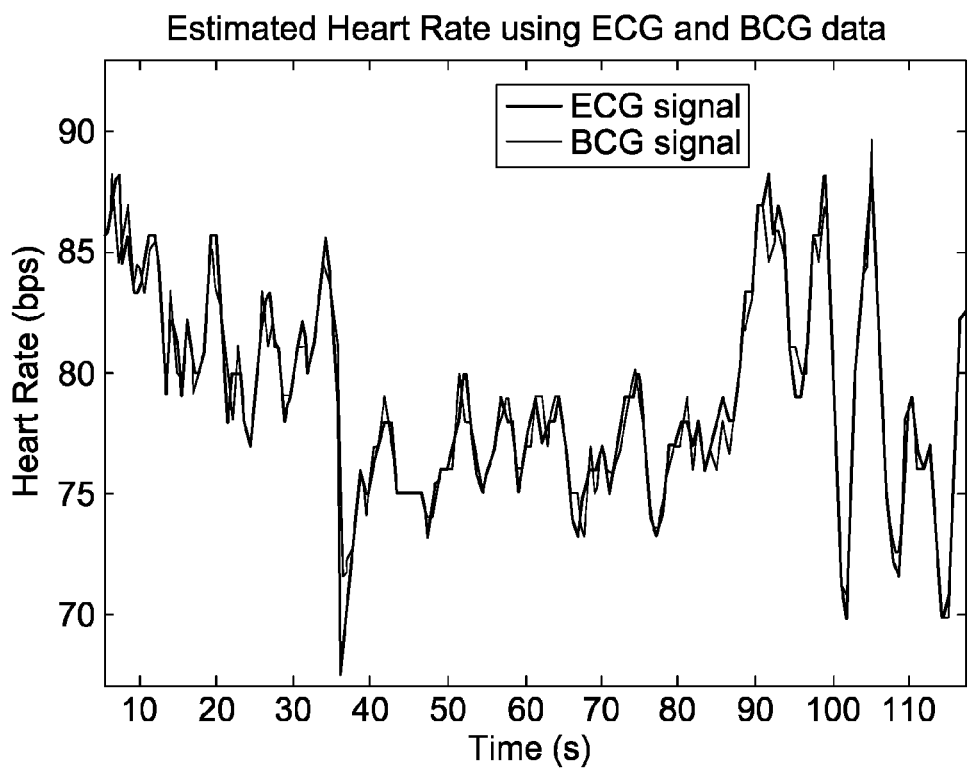

We estimated the heart rate for each subject by applying the adaptive running window algorithm on the BCG signal to detect the peak points and then by measuring the time between two peak points. The estimated heart rate was also averaged using a window of 5 secs to smooth out any irregularities caused by algorithm missing peak points or treating noise as heart beats. FIG. 7 shows the heart rate estimated using the algorithm with a light line and for verifying the efficiency of our algorithm we additionally show with a dark line the heart rate calculated using the ECG signal.

The same technique was applied on all 7 subjects and then we calculated the coefficient of determination R squared between the two datasets using Equation 2. Table 1 shows an average of 0.78, which indicates that our estimated heart rate fits the real heart-rate really well.

$$R^2 = \left(\frac{\text{cov}(bcg, ecg)}{\sqrt{\text{var}(bcg)\text{var}(ecg)}}\right)^2$$

TABLE I

R squared BETWEEN THE BCG AND ECG HEART RATE SIGNALS PER SUBJECT

| | Subject | | | | | | |
|---|---|---|---|---|---|---|---|
| | 1 | 2 | 3 | 4 | 5 | 6 | 7 |
| R squared | 0.63 | 0.49 | 0.94 | 0.97 | 0.80 | 0.76 | 0.90 |

This leads to an average R squared of 0.78 which indicates an excellent agreement between the results provided by embodiments of the invention compared to ECG data.

The device could be used in sports and fitness monitoring, human-computer interaction, entertainment and games by making technology responsive to the physiological state of the user, as well as stress monitoring, relaxation and sleep.

Embodiments of the invention can also allow features of cardiovascular performance and state in a user to be identified that cannot be detected from ECG data, such as pump efficiency and performance of the heart, muscle and valves.

The invention claimed is:

1. A mobile telecommunications device placeable on a chest of a patient arranged for monitoring a heart of the patient, the patient being a human or an animal, the device comprising:
    three motion sensors, each of the motion sensors measuring an effect of a function of the heart and producing a respective motion signal indicative of the effect; and
    a processor adapted and arranged to receive and analyze the motion signals to produce a further motion signal which is independent of an orientation of the device with respect to the chest of the patient, wherein the further motion signal comprises a ballistocardiographic heart signal.

2. The device according to claim 1, wherein the processor is arranged to analyze the motion signals using principle component analysis to produce the further motion signal.

3. The device according to claim 1, wherein at least one of the motion signals includes a breathing component due to a breathing of the patient, the processor being arranged to remove the breathing component from the at least one of the motion signals.

4. The device according to claim 3, wherein the processor is arranged to remove the breathing component using a Savitzky-Golay smoothing algorithm.

5. The device according to claim 1, wherein the processor is arranged to identify heart beats of the heart in the further motion signal.

6. The device according to claim 5, wherein the further motion signal contains maxima and the processor is arranged to identify each of the maxima as representative of one of the heart beats.

7. The device according to claim 6, wherein the maxima are quasi-periodic.

8. The device according to claim 6, wherein the processor is arranged to define a time window of the further motion signal and to scan the time window to identify the maxima in the window.

9. The device according to claim 8, wherein the processor is arranged to identify one of the maxima by defining a cut-off value of the further motion signal and identify a first-occurring peak in the further motion signal above the cut-off value within the time window.

10. The device according to claim 9, wherein the cut-off value is calculated from at least one of: a mean of the further motion signal, a median of the further motion signal, a standard deviation of the further motion signal, and an interquartile range of the further motion signal, within a predetermined period.

11. The device according to claim 9, wherein when a peak has been identified the processor is arranged to shift the time window to a time interval after the identified peak and to identify a next peak in the shifted time window.

12. The device according to claim 11, wherein the shifted time window is arranged to start a predetermined time after the peak.

13. A computer readable medium including instructions which when operated on a smartphone are arranged to cause the smartphone to operate as a device according to claim 1.

14. A method of testing, comprising the steps of: contemporaneously recording an electrocardiographic (ECG) heart signal of a human or animal and a ballistocardiographic (BCG) signal of the human or animal using the device according to claim 1; and comparing the ECG and BCG signals.

15. A method of diagnosis of heart disease in a heart of a patient, comprising the steps of:
    placing a mobile telecommunications device on a chest of the patient, the mobile telecommunications device comprising three motion sensors;
    measuring an effect of a function of the heart using each of the three motion sensors to generate three respective motion signals;
    and analyzing the three motion signals to produce a further motion signal which is independent of an orientation of the device with respect to the chest of the patient, wherein the further motion signal comprises a ballistocardiographic heart signal.

* * * * *